(12) United States Patent
Dahl et al.

(10) Patent No.: US 11,065,287 B2
(45) Date of Patent: Jul. 20, 2021

(54) METHODS OF MODULATING IMMUNE AND INFLAMMATORY RESPONSES VIA ADMINISTRATION OF AN ALGAL BIOMASS

(71) Applicant: Zivo Bioscience, Inc., Keego Harbor, MI (US)

(72) Inventors: Andrew A. Dahl, Bloomfield Hills, MI (US); Amy E. Steffek, Royal Oak, MI (US)

(73) Assignee: ZIVO BIOSCIENCE, INC., Keego Harbor, MI (US)

( * ) Notice: Subject to any disclaimer, the term of this patent is extended or adjusted under 35 U.S.C. 154(b) by 0 days.

(21) Appl. No.: 15/550,749

(22) PCT Filed: Feb. 16, 2016

(86) PCT No.: PCT/US2016/018105
§ 371 (c)(1),
(2) Date: Aug. 11, 2017

(87) PCT Pub. No.: WO2016/133922
PCT Pub. Date: Aug. 25, 2016

(65) Prior Publication Data
US 2018/0021392 A1 Jan. 25, 2018

Related U.S. Application Data

(60) Provisional application No. 62/116,766, filed on Feb. 16, 2015.

(51) Int. Cl.
*A61K 36/05* (2006.01)
*A61K 36/02* (2006.01)
*A61K 9/00* (2006.01)

(52) U.S. Cl.
CPC ............ *A61K 36/05* (2013.01); *A61K 9/0053* (2013.01); *A61K 36/02* (2013.01); *A23V 2200/02* (2013.01); *A23V 2200/324* (2013.01)

(58) Field of Classification Search
None
See application file for complete search history.

(56) References Cited

U.S. PATENT DOCUMENTS

| | | |
|---|---|---|
| 4,012,504 A | 3/1977 | Eckols |
| 4,303,409 A | 12/1981 | Ogawa et al. |
| 4,439,196 A | 3/1984 | Higuchi |
| 4,447,224 A | 5/1984 | DeCant et al. |
| 4,447,233 A | 5/1984 | Mayfield |
| 4,471,055 A | 9/1984 | Opp |
| 4,475,196 A | 10/1984 | La Zor |
| 4,486,194 A | 12/1984 | Ferrara |
| 4,487,603 A | 12/1984 | Harris |
| 4,822,612 A | 4/1989 | Shinpo |
| 4,925,678 A | 5/1990 | Ranney |
| 4,959,217 A | 9/1990 | Sanders |
| 5,167,616 A | 12/1992 | Haak et al. |
| 5,169,383 A | 12/1992 | Gyory et al. |
| 5,225,182 A | 7/1993 | Sharma |
| 5,726,063 A | 3/1998 | Gerard-Monnier et al. |
| 5,767,095 A | 6/1998 | Winget |
| 6,235,495 B1 | 5/2001 | Fu et al. |
| 6,374,874 B1 | 4/2002 | Payne |
| 6,461,607 B1 | 10/2002 | Farmer |
| 6,551,596 B2 | 4/2003 | Kralovec |
| 6,673,908 B1 | 1/2004 | Stanton |
| 6,733,751 B2 | 5/2004 | Farmer |
| 7,025,965 B1 | 4/2006 | Pieloch |
| 7,125,846 B2 | 10/2006 | Rojkjaer |
| 7,807,622 B2 | 10/2010 | Thomas et al. |
| 8,586,053 B2 | 11/2013 | Thomas et al. |
| 8,791,060 B2 | 7/2014 | Thomas et al. |
| 9,486,005 B2 | 11/2016 | Gupta et al. |
| 10,166,270 B2 | 1/2019 | Thomas et al. |
| 10,232,028 B2 | 3/2019 | Dahl |
| 2002/0009479 A1 | 1/2002 | Vardi et al. |
| 2002/0119164 A1 | 8/2002 | Uchiyama et al. |
| 2003/0015587 A1 | 1/2003 | Tsikos et al. |
| 2003/0152587 A1 | 8/2003 | Kralovec |
| 2005/0114920 A1 | 5/2005 | Yusibov et al. |

(Continued)

FOREIGN PATENT DOCUMENTS

| | | |
|---|---|---|
| CA | 2564466 | 12/2005 |
| CA | 2485449 | 4/2006 |

(Continued)

OTHER PUBLICATIONS

USPTO; Advisory Action dated Mar. 6, 2009 in U.S. Appl. No. 11/606,676.

(Continued)

*Primary Examiner* — Jennifer E Graser
(74) *Attorney, Agent, or Firm* — Snell & Wilmer L.L.P.

(57) ABSTRACT

An algal biomass and supernatant derived from at least one species of algae exhibits anti-inflammatory and immune response modulating properties. Methods of reducing the symptoms of or treating a condition or disease in an animal, including bovine mastitis and Bovine Respiratory Disease Complex, and the pain and discomfort caused by osteoarthritis, injury or overexertion or muscle and connective tissue strains, comprises administering to the animal in need thereof an algal biomass or supernatant derived from at least one species of algae, or an extract, derivative or biologically active compound derived from the algae species, biomass or supernatant, or compositions thereof.

14 Claims, No Drawings

(56) References Cited

U.S. PATENT DOCUMENTS

| | | |
|---|---|---|
| 2005/0229585 A1 | 10/2005 | Webster |
| 2005/0260695 A1 | 11/2005 | Flemming et al. |
| 2006/0101803 A1 | 5/2006 | White |
| 2007/0010480 A1 | 1/2007 | Rusing et al. |
| 2007/0207231 A1 | 9/2007 | Thomas et al. |
| 2008/0031863 A1 | 2/2008 | Hildreth et al. |
| 2008/0089843 A1 | 4/2008 | Pillarisetti et al. |
| 2008/0119571 A1 | 5/2008 | Khanna et al. |
| 2008/0272232 A1 | 11/2008 | Cagle et al. |
| 2008/0272615 A1 | 11/2008 | McKnight et al. |
| 2009/0036372 A1 | 2/2009 | Thomas et al. |
| 2009/0117216 A9 | 5/2009 | Thomas et al. |
| 2010/0028488 A1 | 2/2010 | Lo et al. |
| 2011/0081319 A1 | 4/2011 | Thomas et al. |
| 2011/0117122 A1 | 5/2011 | Thomas et al. |
| 2011/0124544 A1 | 5/2011 | He et al. |
| 2011/0143012 A1 | 6/2011 | Rettenmaier |
| 2011/0307976 A1 | 12/2011 | Ploechinger |
| 2012/0328598 A1 | 12/2012 | Gupta et al. |
| 2013/0251698 A1 | 9/2013 | Thomas et al. |
| 2015/0157688 A1 | 6/2015 | Thomas et al. |
| 2016/0120970 A1 | 5/2016 | Dahl et al. |
| 2017/0135391 A1 | 5/2017 | Gupta et al. |
| 2017/0360883 A9 | 12/2017 | Thomas et al. |
| 2018/0255820 A1 | 9/2018 | Dahl |

FOREIGN PATENT DOCUMENTS

| | | |
|---|---|---|
| CA | 2827401 | 8/2011 |
| CN | 102225127 | 10/2011 |
| EP | 1230927 | 8/2002 |
| EP | 1878877 | 1/2008 |
| EP | 1928247 | 10/2009 |
| EP | 2501390 | 9/2012 |
| EP | 2538951 | 1/2013 |
| EP | 3416501 | 12/2018 |
| HK | 1248545 | 10/2018 |
| JP | 0940523 | 2/1997 |
| JP | 2009518312 | 5/2009 |
| JP | 2014006051 | 1/2014 |
| WO | 2011060427 | 5/2001 |
| WO | 2003028749 | 4/2003 |
| WO | 2005112987 | 1/2005 |
| WO | 2006055217 | 5/2006 |
| WO | 2006113925 | 10/2006 |
| WO | 2007065024 | 6/2007 |
| WO | 2011016973 | 2/2011 |
| WO | 2011103569 | 8/2011 |
| WO | 2014201372 | 12/2014 |
| WO | 2017142906 | 8/2017 |
| WO | 2018165205 | 9/2018 |

OTHER PUBLICATIONS

USPTO; Final Office Action dated May 29, 2009 in U.S. Appl. No. 11/606,676.
USPTO; Final Office Action dated Nov. 14, 2008 in U.S. Appl. No. 11/606,676.
USPTO; Office Action dated Feb. 4, 2008 in U.S. Appl. No. 11/606,676.
USPTO; Office Action dated Oct. 8, 2009 in U.S. Appl. No. 11/606,676.
USPTO; Notice of Allowance dated May 27, 2010 in U.S. Appl. No. 11/606,676.
USPTO; Examiner Interview Summary Record dated Apr. 12, 2010 in U.S. Appl. No. 11/606,676.
USPTO; Final Office Action dated Nov. 3, 2008 in U.S. Appl. No. 11/587,266.
USPTO; Non-Final Office Action dated Feb. 4, 2008 in U.S. Appl. No. 11/587,266.
USPTO; Office action dated Oct. 22, 2012 in U.S. Appl. No. 12/067,735.
USPTO; Requirement for Restriction dated Oct. 19, 2010 in U.S. Appl. No. 12/067,735.
USPTO; Requirement for Restriction dated Jul. 20, 2011 in U.S. Appl. No. 12/067,735.
USPTO; Office Action dated Mar. 13, 2012 in U.S. Appl. No. 12/067,735.
USPTO; Final Office Action dated Oct. 23, 2012 in U.S. Appl. No. 12/067,735.
USPTO; Notice of Allowance dated May 13, 2013 in U.S. Appl. No. 12/067,735.
USPTO; Notice of Allowance dated Aug. 15, 2013 in U.S. Appl. No. 12/067,735.
USPTO; Advisory Action dated Feb. 26, 2014 in U.S. Appl. No. 12/897,574.
USPTO; Non-Final Office Action dated Jun. 24, 2013 in U.S. Appl. No. 12/897,574.
USPTO; Final Office Action dated Nov. 13, 2013 in U.S. Appl. No. 12/897,574.
USPTO; Notice of Allowance dated Apr. 8, 2014 in U.S. Appl. No. 12/897,574.
USPTO; Final Office Action dated May 21, 2012 in U.S. Appl. No. 12/947,684.
USPTO; Final Office Action dated Oct. 9, 2013 in U.S. Appl. No. 12/947,684.
USPTO; Office Action dated Sep. 9, 2011 in U.S. Appl. No. 12/947,684.
USPTO; Office Action dated Dec. 20, 2012 in U.S. Appl. No. 12/947,684.
USPTO; Advisory Action dated Aug. 7, 2015 in U.S. Appl. No. 13/804,471.
USPTO; Final Office Action dated Apr. 2, 2015 in U.S. Appl. No. 13/580,471.
USPTO; Office Action dated Aug. 26, 2014 in U.S. Appl. No. 13/580,471.
USPTO; Notice of Allowance dated Jun. 20, 2016 in U.S. Appl. No. 13/580,471.
USPTO; Restriction Requirement dated Mar. 4, 2014 in U.S. Appl. No. 13/580,471.
USPTO; Office Action dated Dec. 8, 2015 in U.S. Appl. No. 13/804,471.
USPTO; Office Action dated Jun. 2, 2014 in U.S. Appl. No. 13/841,739.
USPTO; Office Action dated Jun. 1, 2017 in U.S. Appl. No. 14/558,516.
USPTO; Notice of Allowance dated Jan. 12, 2018 in U.S. Appl. No. 14/558,516.
USPTO; Restriction Requirement dated Dec. 23, 2016 in U.S. Appl. No. 14/558,516.
USPTO; Final Office Action dated May 1, 2017 in U.S. Appl. No. 14/898,091.
USPTO; Office Action dated Jun. 28, 2016 in U.S. Appl. No. 14/898,091.
USPTO; Office Action dated Oct. 3, 2016 in U.S. Appl. No. 14/898,091.
USPTO; Final Office Action dated Jun. 5, 2018 in U.S. Appl. No. 14/898,091.
USPTO; Restriction Requirement dated Dec. 8, 2012 in U.S. Appl. No. 13/397,360.
USPTO; Office Action dated Jun. 19, 2014 in U.S. Appl. No. 13/397,360.
USPTO; Restriction Requirement dated Apr. 20, 2018 in U.S. Appl. No. 15/550,749.
USPTO; Restriction Requirement dated Aug. 6, 2018 in U.S. Appl. No. 15/330,830.
USPTO; Notice of Allowance dated Aug. 27, 2018 in U.S. Appl. No. 14/558,516.
Australia; Examination Report dated Sep. 7, 2012 in AU2006320264.
Australia; Examination Report dated Apr. 11, 2014 in AU2013204257.
Canadian; Examination Report dated Feb. 26, 2015 in CA2631773.
Canadian; Examination Report dated Mar. 31, 2016 in CA2631773.
Canadian; Examination Report dated Apr. 2, 2014 in CA2631773.
Canadian; Examination Report dated May 24, 2013 in CA2631773.
Canadian; Examination Report dated May 16, 2017 in CA2631773.

(56) References Cited

OTHER PUBLICATIONS

Canadian; Examination Report dated Jun. 27, 2018 in CA2631773.
Canadian; Examination Report dated Mar. 28, 2017 in CA2780144.
Canadian; Examination Report dated Aug. 15, 2016 in CA2780144.
EPO; Extended Search Report/Written Opinion dated Nov. 2, 2017 in EP20111745434.
EPO; Examination Report dated Mar. 22, 2012 in EP2006320264.
EPO; Examination Report dated Oct. 13, 2009 in EP2006320264.
EPO; Supplemental Search Report—Written Opinion dated Sep. 9, 2009 in EP2006758513.
EPO; Examination Report dated Nov. 20, 2009 in EP2006758513.
EPO; Examination Report dated Mar. 22, 2012 in EP2006758513.
EPO; Examination Report dated Mar. 31, 2016 in EP2010830908.
EPO; Extended Search Report dated Jun. 2, 2014 in EP20100830908.
EPO; Office Action dated Feb. 23, 2010 in EP2006838974.
EPO; Extended Search Report dated Aug. 10, 2018 in EP16752918.9.
JPO; Examination Report dated Aug. 7, 2012 in JP200854345.
JPO; Examination Report dated Nov. 11, 2014 in JP2012539974.
PCT; Search Report and Written Opinion dated Jul. 29, 2011 in PCT/US2010056862.
PCT; IPRP dated May 22, 2012 in PCT/US2010056862.
PCT; Written Opinion dated Sep. 24, 2014 in PCT/US2014042331.
PCT; International Search Report dated Sep. 24, 2014 in PCT/US2014042331.
PCT; IPRP dated Dec. 15, 2015 in PCT/US2014042331.
PCT; Written Opinion dated May 25, 2017 in PCT/US2017017906.
PCT; International Search Report dated May 25, 2017 in PCT/US2017017906.
PCT; Written Opinion dated Jun. 21, 2011 in PCT/US2011025713.
PCT; International Search Report dated Jun. 21, 2011 in PCT/US2011025713.
PCT; IPRP dated Aug. 28, 2012 in PCT/US2011025713.
PCT; Written Opinion of the International Searching Authority dated Dec. 6, 2005 for Intenational Patent Application No. PCT/US2005/013375.
PCT; International Preliminary Report on Patentability dated Oct. 25, 2006 for International Patent Application No. PCT/US2005/013375.
PCT; Written Opinion of the International Searching Authority dated Mar. 22, 2007 for International Patent Application No. PCT/US2006/015302.
PCT; International Preliminary Report on Patentability dated Oct. 23, 2007 for International Patent Application No. PCT/US2006/015302.
PCT; International Search Report dated Oct. 17, 2007 for International Application No. PCT/US2006/046320.
PCT; International Search Report dated Feb. 23, 2012 for International Application No. PCT/US2011/44786.
PCT; Written Opinion dated Feb. 23, 2012 for International Application No. PCT/US2011/44786.
PCT; IPRP dated Jan. 29, 2013 for International Application No. PCT/US2011/44786.
Amaro et al., "Antimicrobial Activities of Microalgae: An Invited Review," Science Against Microbial Pathogens: Communicating Current Research and Technological Advances (Ed. Mendez-Vilas, A.), Formatex Research Center, Spain, ISBN-13: 978-84-939843-1-1, pp. 1272-1280, (2011).
Bhadury et al., "Exploitation of Marine Algae: Biogenic Compounds for Potential Antifouling Applications," Planta, (E-pub), vol. 219, No. 4, pp. 561-578, (Jun. 24, 2004).
Brewer et al., "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," American Heart Association, vol. 24(24), pp. 1755-1760, (Aug. 19, 2004).
Fujita, "NF-KB: Regulation and Genetic Engineering of Signal Transduction of Inflammation," Journal of Clinical and Experimental Medicine, vol. 190(10), pp. 913-916, (1999).

Kim et al., "Purification and Characterization of a Fibrinolytic Enzyme Produced from *Bacillus* sp.strain CK 11-4 Screened from Chungkook-Jang," Environ. Microbiology, vol. 62, No. 7, pp. 2482-2488, (Jul. 1996).
Kim, Young-Gon, and Moon-Seog Jun, "A Design of User Authentication System Using QR Code Identifying Method," Computer Sciences and Convergence Information Technology (ICCIT), 6th International Conference on IEEE, (Nov. 29-Dec. 1, 2011).
Mudimu et al., "Biotechnological Screening of Microalgal and Cyanobacterial Strains for Biogas Production and Antibacterial and Antifungal Effects," Metabolites, vol. 4, No. 2, pp. 373-393, (May 15, 2014).
Noda et al., "A Water-Soluble Antitumor Glycoprotein from Chlorella Vulgaris," Faculty of Pharmaceutical Sciences, Kyushu University, (Oct. 1996) Abstract Only.
Oben et al., "The Effects of ProAlgaZyme Novel Algae Infusions on Metabolic Syndrome and Markers of Cardiovascular Health," Lipids in Health and Disease, vol. 6, pp. 1-9, (2007).
Oben et al., "Lipids in Health and Disease: The Effects of ProAlgaZyme Novel Algae Infusion of Metabolic Syndrome and Markers of Cardiovascular Health," BioMed Central, pp. 1-9, (Sep. 5, 2007).
Okada et al., "Inflammatory Bowel Disease and Cytokine," Journal of Clinical and Experimental Medicine, pp. 265-268, (Oct. 2004).
Press Release entitled, "Western Glory Hole Inc. Enters Definitive Agreement with Health Enhancement Products in," Business Wire, (Oct. 30, 2003).
Sarkar et al., "Using Chemopreventive Agents to Enhance the Efficacy of Cancer Therapy," Cancer Research, vol. 66(7), pp. 3347-3350, (Apr. 1, 2006).
"BioSuperfood-Algae/Spirulina for People," Optimum Choices, pp. 1-23, http://www.optimumchoices.com/spirulina.htm., (Apr. 14, 2010).
"Spirulina," MedlinePlus, U.S. National Library of Medicine and the National Institutes of Health, http://www.nlm.nih.gov/medlineplus/druginfo/natural/patient-spirulina.html., (Apr. 14, 2010).
Gupta et al., "ProAlgaZyme and its Sub-Fractions Increase Plasma HDL-Cholesterol via Up Regulation of ApoA1, ABCA1 and SRB1 and Inhibition of CETP in Hypercholesterolemic Hamsters," Journal of Nutrition and Food Science, WSU, (Jun. 2012).
www.michaelkiriac.com, (Jan. 1, 2003).
"Research Indicates ProAlgaZyme May Decrease Risk of Stroke or Heart Attack," Supplemental Quality.com, pp. 10, 11, (Jan. 20, 2004).
USPTO; Notice of Allowance dated Oct. 29, 2018 in U.S. Appl. No. 14/898,091.
Canadian; Examination Report dated Mar. 29, 2018 in CA2827401.
EPO; Supplementary Search Report dated Aug. 28, 2018 in EP16752918.9.
EPO; Extended Search Report dated Oct. 8, 2018 in EP16752918.9.
PCT; International Preliminary Report on Patentability dated Aug. 21, 2018 in PCT/US2017/017906.
PCT; International Search Report dated Jun. 28, 2018 in International Application No. PCT/2018/021215.
PCT; Written Opinion dated Jun. 28, 2018 in International Application No. PCT/US2018/021215.
FDA, "Data Standards Manual: Route of Administration," www.fda.gov/Drugs/DevelopmentApprovalProcess/FormsSubmissionRequirements.gov, (Revised Jan. 11, 2006).
USPTO; Non-Final Office Action dated Apr. 19, 2019 in U.S. Appl. No. 15/330,830.
USPTO; Non-Final Office Action dated Mar. 11, 2019 in U.S. Appl. No. 16/273,794.
EPO; Examination Report dated Feb. 22, 2019 in Application No. EP11745434.
Solomon et al., "Midlife Serum Cholesterol and Increased Risk of Alzheimer's and Vascular Dementia Three Decades Later," Dementia and Geriatric Cognitive Disorders, vol. 28(1), pp. 75-80, (Aug. 2009).
Li et al., "Inactivation of Nuclear Factor kB by Soy Isoflavone Genistein Contributes to Increased Apoptosis Induced by Chemotherapeutic Agents in Human Cancer Cells," Cancer Research, vol. 65(15), pp. 6934-6942, (2005).

METHODS OF MODULATING IMMUNE AND INFLAMMATORY RESPONSES VIA ADMINISTRATION OF AN ALGAL BIOMASS

CROSS REFERENCE TO RELATED APPLICATIONS

This application claims priority to U.S. Provisional Patent Application Ser. No. 62/116,766 filed Feb. 16, 2015, which is incorporated herein by reference in its entirety.

FIELD OF THE INVENTION

The present invention relates to methods of modulating immune responses and inflammatory responses in animals and in particular relates to an algal biomass having anti-inflammatory and autoimmune modulating properties and methods of treating bovine mastitis and other diseases in animals by administering same.

BACKGROUND OF THE INVENTION

Inflammation is a biological response to the presence of a harmful or irritating substance on, or in, the body of an animal, and is a method of self-protection by the immune system. Inflammation can be acute, starting rapidly and quickly becoming severe, or it can be chronic and last several months or years. Symptoms of inflammation include pain, heat, redness, swelling, and loss of function of certain parts of the body at the site of inflammation.

Typical treatments for inflammation can include non-steroidal anti-inflammatory drugs (NSAIDs), acetaminophen, corticosteroids, and immune selective anti-inflammatory derivatives (ImSAIDs).

Immunotherapy modulates an individual's immune system in order to treat diseases caused by an immune response. Immunotherapies can include cytokines and interleukins, and can be used to treat cancer, manage organ transplantation, treat autoimmune diseases, treat immune tolerance, and treat allergies. For example, chemokines, a subclass of cytokines, are small signaling proteins secreted by cells in response to various disease states. Diseases that are characterized by chronic inflammation, such as rheumatoid arthritis, psoriasis, and inflammatory bowel diseases, can be treated with immunomodulators. However, some immunomodulators may require months for any beneficial effects to manifest, and some may have adverse effects on internal organs, such as the liver and kidneys.

There are also many diseases that occur in non-human animals of all species, and especially in dairy cows, involving inflammation, or the immune system in general, which cost the livestock industry both in terms of lost animals and cost of treatment. These diseases include bovine mastitis and Bovine Respiratory Disease Complex (BRDC, also known as Shipping Fever), amongst others. Bovine mastitis is caused by pathogens that invade udder tissue and start an infection therein. Infectious agents can also spread from cow to cow by the hands of milkers or the milking equipment that touches the udders. BRDC commonly occurs in beef and dairy cows after weaning, when the cows are grouped together and shipped (hence the name Shipping Fever). Many different pathogens can cause BRDC, and many other factors such as stress and feeding can contribute to the disease. Current treatments for each of these diseases can include (depending on the source of the disease) anti-infectious agents, anti-parasitic agents, non-steroidal anti-inflammatories, bronchodilators, mucolytic agents, and oral rehydration fluids.

Another inflammatory disease, osteoarthritis, occurs in many animals, both human and non-human, and is especially prevalent in companion animals, such as cats and dogs. It is caused by deterioration of cartilage surrounding the joints that leads to chronic joint inflammation and pain. This can cause a decreased range of motion in the body and can especially effect walking. Treatments can include anti-inflammatories in order to reduce swelling and pain, and hot and cold therapy.

Many of the above-mentioned treatments for various animal inflammatory and auto-immune related diseases can result in unwanted side effects and, therefore, there remains the need for anti-inflammatory and auto-immune modulating compounds that are effective and safe. Especially needed are new and more effective treatments for bovine mastitis, bovine respiratory disease complex, transition cow syndrome, canine osteoarthritis, canine skeletal-muscular over-exertion and porcine reproductive and respiratory syndrome virus immune disorder, (PRRSV), amongst others.

SUMMARY OF THE INVENTION

In various embodiments, an algal biomass and a supernatant, derived from at least one species of algae, exhibit inflammatory and/or immune response modulating properties. An exemplary algal biomass and supernatant may be obtained by processing the biological material of NCMA Deposit # PATENT201602001.

In other aspects, an anti-inflammatory and immune response modulating composition comprises an algal biomass or a supernatant derived from at least one species of algae. An exemplary algal biomass and supernatant may be obtained by processing the biological material of NCMA Deposit # PATENT201602001.

In various embodiments, a method of producing an algal biomass and a supernatant, each exhibiting anti-inflammatory and/or immune response modulating properties, comprises obtaining a sample of the biological material of NCMA Deposit # PATENT201602001 and separating the cellular matter from the liquid present therein.

The present disclosure also provides methods for treating or preventing a disorder in an animal, human or non-human, by administering to the animal a therapeutically effective amount of an algal biomass or supernatant derived from at least one species of algae, or an extract, derivative, or biologically active compound derived therefrom, or a composition thereof Further, a method of treating inflammation in an animal comprises administering to the animal in need thereof a therapeutically effective amount of an algal biomass or supernatant derived from at least one species of algae. In various embodiments, said animal in need of treatment thereof is a beef or dairy cow, a dog, a cat, a horse, a goat, a pig, any other livestock, or a human.

In other aspects of the invention, a method of treating inflammation in an animal comprises administering to the animal in need thereof a therapeutically effective amount of a composition comprising an algal biomass or supernatant derived from at least one species of algae. In various embodiments, said animal in need of treatment thereof is a beef or dairy cow, a dog, a cat, a horse, a goat, a pig, any other livestock, or a human.

A method of modulating an immune response and/or an inflammatory response in an animal comprises administering to the animal in need thereof a therapeutically effective amount of an algal biomass or supernatant derived from at least one species of algae. In various embodiments, said animal in need of treatment thereof is a beef or dairy cow, a dog, a cat, a horse, a goat, a pig, any other livestock, or a human.

In further aspects, a method of modulating an immune response and/or an inflammatory response in an animal comprises administering to the animal in need thereof a therapeutically effective amount of a composition comprising an algal biomass or supernatant derived from at least one species of algae. In various embodiments, said animal in need of treatment thereof is a beef or dairy cow, a dog, a cat, a horse, a goat, a pig, any other livestock, or a human.

The invention also provides a method of modulating the autoimmune system in an animal comprising administering to the animal in need thereof a therapeutically effective amount of an algal biomass or supernatant derived from at least one species of algae. In various embodiments, said animal in need of treatment thereof is a beef or dairy cow, a dog, a cat, a horse, a goat, a pig, any other livestock, or a human.

Furthermore, a method of modulating the autoimmune system in an animal comprises administering to the animal in need thereof an effective amount of a composition comprising an algal biomass or supernatant derived from at least one species of algae. In various embodiments, said animal in need of treatment thereof is a beef or dairy cow, a dog, a cat, a horse, a goat, a pig, any other livestock, or a human.

In further aspects of the invention, a method for supporting a healthy immune system in an animal comprises administering to the animal in need thereof a therapeutically effective amount of an algal biomass or supernatant derived from at least one species of algae. In various embodiments, said animal in need of treatment thereof is a beef or dairy cow, a dog, a cat, a horse, a goat, a pig, any other livestock, or a human.

Also, a method for supporting a healthy immune system in an animal comprises administering to the animal in need thereof a therapeutically effective amount of a composition comprising an algal biomass or supernatant derived from at least one species of algae. In various embodiments, said animal in need of treatment thereof is a beef or dairy cow, a dog, a cat, a horse, a goat, a pig, any other livestock, or a human.

The present disclosure also provides a method of treating bovine mastitis comprising administering to the animal in need thereof a therapeutically effective amount of an algal biomass or supernatant derived from at least one species of algae. In various embodiments, said animal in need of treatment thereof is a cow.

In other embodiments, a method of promoting a healthy, robust immune response to the presence of pathogens in the mammary duct or within the mammary gland of an animal comprises administering to the animal in need thereof a therapeutically effective amount of an algal biomass or supernatant derived from at least one species of algae. In various embodiments, said animal in need of treatment thereof is a cow.

In further aspects of the invention, a method of treating bovine respiratory disease complex in an animal comprises administering to the animal in need thereof a therapeutically effective amount of an algal biomass or supernatant derived from at least one species of algae. The animal in need of treatment thereof may be a cow.

Also, a method of reducing pain and/or discomfort in an animal caused by osteoarthritis, slight to moderate injury or overexertion, or muscle and connective tissue strains comprises administering to the animal in need of treatment thereof a therapeutically effective amount of an algal biomass or supernatant derived from at least one species of algae. In various embodiments, said animal in need of treatment thereof is a beef or dairy cow, a dog, a cat, a horse, a goat, a pig, any other livestock, or a human.

The invention also provides for a method of reducing pain and/or discomfort in an animal caused by osteoarthritis, slight to moderate injury or overexertion, or muscle and connective tissue strains comprising administering to the animal in need of treatment thereof a therapeutically effective amount of a composition comprising an algal biomass or supernatant derived from at least one species of algae. In various embodiments, said animal in need of treatment thereof is a beef or dairy cow, a dog, a cat, a horse, a goat, a pig, any other livestock, or a human.

DETAILED DESCRIPTION OF THE INVENTION

In various embodiments of the present disclosure, an algal biomass or supernatant, derived from a single algal species or multiple algae species, exhibits anti-inflammatory and/or autoimmune modulation properties. Also disclosed are methods of treating inflammation and/or modulating the inflammatory and/or immune response in an animal comprising administering to the animal in need thereof a therapeutically effective amount of an algal biomass or supernatant derived from at least one species of algae. In various embodiments, a method comprises administering to an animal in need thereof a therapeutically effective amount of a composition comprising an algal biomass or supernatant derived from at least one species of algae. In other aspects, a method comprises administering a therapeutically effective amount of an extract, derivative or biologically active compound derived from at least one species of algae, or derived from an algal biomass or supernatant further derived from at least one species of algae, to an animal in need thereof. Further, the animal in need thereof is a beef or dairy cow, a dog, a cat, a horse, a goat, a pig, any other livestock, or a human. In various embodiments, the animal in need thereof is a beef or dairy cow, or a dog. The animal in need thereof may also be human. In various embodiments, the at least one species of algae comprises a *klebsormidium* species of algae.

The term "animal" is used herein to refer to all animals, human or otherwise. In some instances, the term "non-human animal" may be used to distinguish from human animals. In various embodiments, the term "animal" may refer to, for example, a beef or dairy cow, a dog, a cat, a bird, a fish, a horse, a goat, a sheep, a pig, various other livestock animals, or a human. In various embodiments, the term "animal" refers to common agricultural livestock animals such as bovine, porcine, and poultry, and the like.

Algal biomass and supernatant from algae; and extracts, derivatives and biologically active compounds derived from algae and/or from an algal biomass:

The term "algal biomass" is used herein to generally refer to cellular material (e.g. whole algal cells) derived from naturally occurring or genetically modified algae ("GMO algae"). For example, in various embodiments, an algal biomass comprises freeze-dried or otherwise desiccated algae of one or more species of algae. In various embodiments, an algal biomass may comprise powdered or granulated desiccated algae from one or more species. In various embodiments, an algal biomass is derived from a *klebsor-*

*midium* species of algae by freeze-drying the cellular material and optionally powdering, milling or otherwise granulating the cellular material obtained upon drying. In various embodiments, an algal biomass is obtained by processing the biological material of NCMA Deposit # PATENT201602001, such as by draining and/or compressing it to remove liquid components (the "supernatant") and then freeze-drying the remaining cellular material.

In various aspects of the invention, an algal biomass comprises whole algal cells of one or more algal cultures grown in distilled water supplemented with various sterilized materials. A deposit of biological material that may be used to obtain an algal biomass and supernatant in accordance to the present disclosure was originally deposited on Oct. 6, 2006 at the Provasoli-Guillard National Center for Marine Algae and Microbiota—Bigelow Laboratory for Ocean Sciences, (NCMA), 60 Bigelow Drive, East Boothbay, Me., 04544, U.S.A., and assigned by the International Depositary Authority accession # PATENT201602001. This deposit is available to the public upon grant of a patent disclosing the same. This deposit was made pursuant to 37 C.F.R. § 1.808 and MPEP § 2410.01 and, therefore, access to the deposit will be available during pendency of this application making reference to the deposit to one determined by the Commissioner to be entitled thereto under 37 C.F.R. § 1.14 and 35 U.S.C. § 122 and with one exception, that all restrictions imposed by the depositor on the availability of the deposited biological material to the public be irrevocably removed upon the granting of the patent.

A method of producing an algal biomass or a supernatant having anti-inflammatory and/or immune response modulating properties may comprise obtaining a sample of the biological material of NCMA Deposit # PATENT201602001 and separating the solid and liquid components to obtain the algal biomass and supernatant respectively.

In various embodiments, an algal biomass is formulated into a composition comprising the algal biomass, such as, for example, by suspending or milling the algal biomass in vegetable oil or other vehicle to form a paste. These aspects are discussed in more detail below.

In other aspects, a supernatant is obtained during the process of drying at least one algae species to produce an algal biomass. In various embodiments, a supernatant obtained from wet algae (e.g. by simply compressing the wet algae in a press or allowing the liquid to drain therefrom) exhibits anti-inflammatory and/or immune response modulating properties that may be identical, partly similar, or entirely different from the properties exhibited by the algal biomass. Also, drying of at least one species of algae produces two separate biologically active materials, namely, a supernatant and an algal biomass. In various embodiments, a supernatant derived from the drying of at least one species of algae is concentrated down (e.g. by evaporative removal of water and other volatiles) to a syrup or other concentrate. For example, a supernatant may be concentrated down to a golden yellow syrup that exhibits anti-inflammatory and/or immune response modulating properties. In various aspects of the invention, a supernatant and an algal biomass are both obtained from a *klebsormidium* species of algae by compressing the liquid from the *klebsormidium* species of algae to obtain the supernatant and, optionally, further desiccating the remaining solid plant material to produce the algal biomass.

A supernatant may be produced by obtaining a sample of the biological material of NCMA Deposit # PATENT201602001 and draining off the liquid under gravity flow. The liquid thus obtained is termed the "supernatant."

In other embodiments, a sample of the biological material of NCMA Deposit # PATENT201602001 is physically compressed to squeeze out supernatant from the cellular material. The solid matter left behind in either of these mechanical processes is an algal biomass in accordance to the present disclosure.

In various embodiments, an algal biomass is starting material for various extracts, derivatives, and biologically active compounds therefrom. In other variations, an algal biomass is manipulated, such as solvent extracted, to provide any number of extracts, derivatives and/or biologically active compounds from the starting algal biomass. Further, the solvent extracts from an algal biomass may be further manipulated, such as by high-pressure liquid chromatography (HPLC) or distillation to obtain individual biologically active compounds or mixtures of biologically active compounds. For example, in various embodiments an algal biomass is solvent extracted and the combined extracts subjected to HPLC to isolate various flavonoids, phytohormones, fatty acids, polysaccharides, or other materials, or mixtures thereof that were naturally occurring in the algal biomass. Manipulation of the algal biomass may change the nature (e.g. chemical structure) of one or more of the constituents in the algal biomass such that one or more compounds are isolated that were not naturally occurring in the starting algal biomass. For example, manipulation of an algal biomass may result in isolation of compounds that are derivatives of compounds naturally occurring in the starting algae (e.g. a salt of a naturally occurring carboxylic acid, or a cyclic anhydride from a naturally occurring dicarboxylic acid, or a denatured protein, and so forth).

In an aspect of the invention, one or more of an extract, derivative, and biologically active compound derived from an algal biomass further derived from at least one species of algae exhibits anti-inflammatory and/or immune response modulating properties. One or more of an extract, derivative, and biologically active compound may be derived from an algal biomass derived from a *klebsormidium* species of algae, wherein the one or more of an extract, derivative, and biologically active compound exhibits anti-inflammatory and/or immune response modulating properties.

In further aspects, an algal biomass is derived from the genus *Klebsormidium*. *Klebsormidium* is a genus of filamentous charophyte green algae of 20 known species, including *K. acidophilum*, *K. bilatum*, *K. crenulatum*, *K. dissectum*, *K. drouetii*, *K. elegans*, *K. flaccidum*, *K. fluitans*, *K. fragile*, *K. klebsii*, *K. lamellosum*, *K. montanum*, *K. mucosum*, *K. nitens*, *K. pseudostichococcus*, *K. scopulinum*, *K. sterile*, *K. subtile*, *K. subtilissimum*, and *K. tribonematoideum*. In various embodiments, an algal biomass is derived from any presently known, or yet to be discovered, species of *Klebsormidium* algae.

For example, an algal biomass may be derived from an algae species selected from the group consisting of *K. acidophilum*, *K. bilatum*, *K. crenulatum*, *K. dissectum*, *K. drouetii*, *K. elegans*, *K. flaccidum*, *K. fluitans*, *K. fragile*, *K. klebsii*, *K. lamellosum*, *K. montanum*, *K. mucosum*, *K. nitens*, *K. pseudostichococcus*, *K. scopulinum*, *K. sterile*, *K. subtile*, *K. subtilissimum*, *K. tribonematoideum*, and mixtures thereof.

In other examples, an algal biomass is derived from algae species selected from the group consisting of *klebsormidium nitens*, *klebsormidium flaccidum*, and mixtures thereof. In other aspects, an algal biomass is derived from *klebsormidium nitens*. Further, an algal biomass may be derived from *klebsormidium flaccidum*.

In some instances, an algal biomass is used in its raw form, i.e. as a wet mass of cellular material, or in a further processed form. For example, the algal biomass can be processed to extract water-soluble or solvent-soluble contents, then concentrated, and sterilized. In various other embodiments, algal biomass in its raw form is simply loaded into a syringe and distributed into the mouth of an animal as a food supplement.

Furthermore, an algal biomass can be processed to remove cellular cytoplasmic material and cell walls to leave behind what are primarily mixtures comprising algal flavonoids, phyto-hormones, fatty acids, polysaccharides, and the like. Different forms (e.g. raw or further processed as described, etc.) may be desired depending on the desired dosage form, route of administration, animal type, therapeutic effect sought, and other considerations.

Methods of Treatment:

As used herein, the term "therapeutically effective amount" in the context of administering an algal biomass, a supernatant, or compositions thereof, to an animal in need thereof, and in the context of administering at least one of an extract, derivative and biologically active compound derived from an algal species or algal biomass, or compositions thereof, to an animal in need thereof, refers to a sufficient amount of the administered material to provide a desired prophylactic or therapeutic effect, and takes into account both the dose and dosage regimen. A prophylactic effect can manifest as maintaining a healthy condition for an animal. In various embodiments, a therapeutically effective amount is that amount which keeps an animal or herd of animals in a healthier condition compared to animals not receiving an algal derived supplement.

For example, a "therapeutically effective amount" of supernatant for the treatment of bovine mastitis in a dairy cow may be from about 0.001 mL to about 100 mL per day administered by intramammary injection per quarter immediately following each milking for eight days. In another non-limiting example, a "therapeutically effective amount" of algal biomass for the modulation of an inflammatory response in an animal may be from 0.5 ounces to about 5 ounces per day, orally feed to the animal each day for eight days. Further examples of therapeutically effective amounts are provided herein below.

In various embodiments, the methods of treatment in accordance with the present disclosure are applicable to any animal in need of treatment thereof. Examples of animals suitable as subjects for treatment according to the present methods include, but are not limited to, bovine animals (e.g. beef and dairy cattle), ovine animals, caprine animals, camelids, equidae, goats and other ruminant animals, porcine animals, and other livestock animal commercial or otherwise, canine animals including domestic dogs, feline animals including domestic cats, ursine animals, primates, mammals in general, and human animals.

An algal biomass or supernatant derived from at least one algal species, or any one of an extract, derivative and biologically active compound derived from at least one species of algae or from an algal biomass, or compositions comprising any of the foregoing, may be administered to the animal in need of treatment thereof via any route of administration, in any suitable dosage form, and in accordance to any treatment regimen.

Routes of administration includes, but are not limited to, oral, sublingual, buccal, nasal, intrasinal, mucosal, ophthalmic, conjunctival, parenteral, intravenous, intramuscular, intralymphatic, intraductal, rectal, vaginal, topical, and transmammary (e.g. intramammary infusion). In various embodiments, a route of administration is chosen from the group consisting of orally, subcutaneously, parenterally including intravenous, intraarterial, intramuscular, intraperitoneally, intratonsillar, intranasal, intramammary, intrathecal and infusion. In other embodiments, administration comprises direct application of any of the above-mentioned materials to skin or epithelial cells, such as those found in the ducts of mammary glands, or any opening of the mammalian body to the environment where epithelial cells are present. A more complete listing of "Route of Administration" is found on the U.S. FDA website at www.fda.gov, the list "Route of Administration" for a drug substance is incorporated herein by reference.

In various embodiments, suitable dosage forms relate to the nature of the material to be administered (e.g. dried algal biomass, supernatant from algae, etc.), route of administration, the type of animal in need of treatment, and the treatment regimen, and include, but are not limited to, loose powders and granulates, pellets, pills, tablets, capsules, drops, ointments, pastes, emulsions (W/O, O/W), suspensions, creams, foams, pomades, injectable liquids, patches, suppositories, devices and implants. In various embodiments, a base algal derived material, (e.g. a concentrated supernatant in syrup form, having been derived from compressing algae plant material to produce a supernatant and evaporation of volatiles from the supernatant to produce syrup) may be diluted in a sterile saline buffer or other sterile diluent to produce an injectable liquid or a liquid suitable for infusion. An algal biomass, (in a dry state, e.g. after the freeze-drying of algal plant material), may be packed into a capsule shell, ground to a powder, placed into the mouth of an animal, added to livestock feed, or compounded with a vehicle to produce an oral paste, or a transdermal, rectal or vaginal paste, emulsion or cream. An algal biomass, a supernatant, an extract, a derivative, or a biologically active compound derived from any of the previous, may be further compounded into a pharmaceutical composition having any number, type and quantity of excipients (e.g. water, solvent, emulsifiers, dispersants, fillers, disintegrants, buffers, thickeners, surfactants, emollients, stabilizers, preservatives, colorants, flavors, etc.) to produce a desired and usable final dosage form. In various embodiments, the dosage form is a sterile injectable or infusible liquid, or a paste, or a wet suspension that can be loaded into the mouth of an animal.

A desired fluidity for the material being administered in accordance to the present disclosure can be maintained, for example, by the use of a diluent, emulsifier or suspending agent, e.g. for example water or lecithin, or by the use of a particular particle size in the case of dispersions, or by the use of surfactants or other additives. Non-aqueous vehicles such a cottonseed oil, sesame oil, olive oil, soybean oil, corn oil, sunflower oil, or peanut oil, and various esters, such as isopropyl myristate, may also be used as solvent systems for the compositions herein. Additionally, various additives which enhance the stability, sterility, and isotonicity of the compositions, including antimicrobial preservatives, antioxidants, chelating agents, and buffers, can be added. Various antibacterial and antifungal agents include, for example, parabens, chlorobutanol, phenol, sorbic acid, and the like. In various embodiments, compositions in accordance to the present disclosure further comprise isotonic agents, for example, sugars, sodium chloride, and the like. In various embodiments, a prolonged absorption of an injectable dosage form can be brought about by the use of agents delaying absorption, for example, aluminum stearate and gelatin.

An algal biomass, supernatant, extract, derivative, or biologically active compound from at least one algae species may be administered parenterally to the patient in the form of slow-release subcutaneous implants or targeted delivery systems, such as via monoclonal antibodies, vectored delivery, iontophoretic, polymer matrices, liposomes, and/or microspheres. Examples of delivery systems that may find use herein are further disclosed in the following U.S. Pat. Nos.: 5,225,182; 5,169,383; 5,167,616; 4,959,217; 4,925,678; 4,487,603; 4,486,194; 4,447,233; 4,447,224; 4,439,196; and 4,475,196.

Administration of an algal biomass, its extracts or isolates in accordance with the disclosure can be orally, such as in a raw of processed form. Alternatively, administration can be topically and the aseptic extracts or isolates of the algal biomass (but not the algal biomass itself) can be applied directly to skin or epithelial cells, such as those found in the ducts of mammary glands, or any opening of the mammalian body to the environment where epithelial cells are present. Other dosage forms can include oral (with further processing to remove cellular material) or parenteral (with any necessary sterilization).

In various embodiments, suitable treatment regimens include, but are not limited to, a single dosage (e.g. a one-time pill or injection), more than one dose, at least one dosage per day for more than a day, daily addition to animal feed, and the like. Treatment regimens may commence at the first sign of a symptom in an animal, or at any other time, such as for prophylactic treatment. Also, doses can be single doses or multiple doses over a period of several days. In various embodiments, a treatment has a length proportional to the length of the disease process, the effectiveness of the particular algal material, and the animal species being treated. For administering compounds of the present disclosure parenterally, they can generally be formulated in a unit dosage injectable form (solution, suspension, emulsion). Pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

An algal biomass or a supernatant derived from at least one species of algae, or an extract, derivative or biologically active substance obtained therefrom, may be used to reduce the symptoms of, or in some cases, treat any condition or disease characterized by any symptom of inflammation or a loss of function such as, but not limited to, acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, and multiple sclerosis.

A method of reducing the symptoms of and/or treating a condition or disease in an animal characterized by inflammation or a loss of function comprises administering to the animal in need thereof a therapeutically effective amount of an algal biomass derived from at least one species of *klebsormidium*. In various embodiments, the condition or disease thus treated is chosen from the group consisting of acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, multiple sclerosis, and combinations thereof.

A method of reducing the presence of and/or treating inflammation in an animal comprises administering to the animal in need thereof a therapeutically effective amount of an algal biomass derived from at least one species of algae. In various embodiments, the animal in need of treatment thereof is a beef or dairy cow, a dog or a human. In various embodiments, the at least one species of algae comprises a *klebsormidium* species of algae. In various embodiments, the at least one species of algae is selected from the group consisting of *klebsormidium nitens, klebsormidium flaccidum,* and mixtures thereof. In various embodiments, the at least one species of algae comprises *klebsormidium nitens*. In various embodiments, the at least one species of algae comprises *klebsormidium flaccidum*.

Furthermore, a method of reducing the presence of and/or treating inflammation in an animal comprises administering to the animal in need thereof a therapeutically effective amount of a composition comprising an algal biomass derived from at least one species of algae. In various embodiments, the animal in need of treatment thereof is a beef or dairy cow, a dog or a human. In various embodiments, the at least one species of algae comprises a *klebsormidium* species of algae. In various embodiments, the at least one species of algae is selected from the group consisting of *klebsormidium nitens, klebsormidium flaccidum,* and mixtures thereof. In various embodiments, the at least one species of algae comprises *klebsormidium nitens*. In various embodiments, the at least one species of algae comprises *klebsormidium flaccidum*.

A method of modulating the autoimmune system of an animal comprises administering to the animal in need thereof a therapeutically effective amount of an algal biomass derived from at least one species of algae. In various embodiments, the at least one species of algae is selected from the group consisting of *klebsormidium nitens, klebsormidium flaccidum,* and mixtures thereof. In other embodiments, the at least one species of algae comprises *klebsormidium nitens*. In further embodiments, the at least one species of algae comprises *klebsormidium flaccidum*.

An algal biomass derived from at least one species of algae can stimulate production of certain chemokines (such as, for example, KC and IL-8); inhibits or attenuates certain pro-inflammatory cytokines (such as, for example, TNF-α, IL-1β, IL-2 and IL-6); and/or promotes various anti-inflammatory cytokines.

There are numerous cytokines, such as interleukins ("IL") produced by white blood cells. Individual interleukins include, for example, IL-2, IL-10, and IL-17A. Each of these interleukins have specific functions and effects, such as decreasing or increasing inflammation, stimulating the proliferation and function of various cell types, and regulating the production of antibodies. For example, IL-2 contributes toward inflammation and may be considered as inflammatory proteins, while IL-10 may be considered an anti-inflammatory protein that decreases inflammation. Therefore, the more IL-2 produced, the greater the inflammation and the more IL-10 produced the lesser the inflammation.

The chemokine KC, also called CXCL1, is a small cytokine within the CXC family that plays a role in the processes of angiogenesis, inflammation, wound healing and tumorigenesis. Interleukin 8 (or IL-8) is also a chemokine, known to induce chemotaxis in target cells and induce phagocytosis. It is also implicated in bronchiolitis.

Cytokines include tumor necrosis factor (TNF) alpha, or TNF-α, which is involved in the regulation of immune cells.

Further, elevated production of TNF-α has been implicated as a contributing factor in a variety of human diseases, including cancer. TNF-α contributes to inflammation and may be considered an inflammatory protein. The more TNF-α produced, the greater the inflammation.

Methods of Treating Bovine Mastitis:

In various embodiments, a method of treating bovine mastitis in a dairy cow comprises administering to the animal in need thereof a therapeutically effective amount of an algal biomass derived from at least one species of algae. Also, a method of treating bovine mastitis in a dairy cow comprises administering to the animal in need thereof a therapeutically effective amount of a composition comprising an algal biomass derived from at least one species of algae. In various embodiments, a method of treating bovine mastitis in a dairy cow comprises administering to the animal in need thereof a therapeutically effective amount of a supernatant obtained from drying at least one species of algae. Also, a method of treating bovine mastitis in a dairy cow comprises administering to the animal in need thereof a therapeutically effective amount of at least one of an extract, derivative and biologically active compound derived from an algal biomass further derived from at least one species of algae. In various embodiments, the at least one species of algae comprises a *klebsormidium* species of algae. In various embodiments, the at least one species of algae is selected from the group consisting of *klebsormidium nitens, klebsormidium flaccidum,* and mixtures thereof. In various embodiments, the at least one species of algae comprises *klebsormidium nitens*. In other aspects, the at least one species of algae comprises *klebsormidium flaccidum*.

Administration of a therapeutically effective amount of an algal biomass or supernatant derived from at least one species of algae, or administration of a therapeutically effective amount of at least one of an extract, derivative and biologically active substance derived therefrom to a dairy cow in need thereof can promote a healthy, robust immune response to the presence of pathogens in the mammary duct or within the mammary gland itself that causes mastitis.

Bovine mastitis is an inflammatory reaction of udder tissue and functional loss of mammary gland production, and often cell necrosis due to a pathogenic (generally bacterial) infection and can be chronic or acute in nature, and sometimes fatal to dairy cows. The infection can be caused by a source such as, but not limited to, *Pseudomonas aeruginosa, Staphylococcus aureus, Staphylococcus epidermidis, Streptococcus agalactiae, Streptococcus uberis, Brucella melitensis, Corynebacterium bovis, Mycoplasma bovis, Escherichia coli, Klebsiella pneumonia, Klebsiella oxytoca, Enterobacter aerogenes, Pasteurella spp., Trueperella pyogenes, Proteus spp., Prototheca zopfii,* or *Prototheca wickerhamii*.

In bovine mastitis, an efficient and rapid, but not overwhelming, immune response is appropriate and necessary to eradicate infection in the animal. However, prolonged elevation of various immune markers, (such as TNF-α, IL-1β and IL-6) can result in harm to tissue, leading to severe losses in milk production and potentially chronic cases of infection. One issue with continued increases in these and other cytokines is that mammary epithelial cells will undergo extensive apoptosis. Continued elevation of immune markers is similar to what is seen when a cow is dried off during mammary gland involution, which can end up causing reduced milk production and subsequently a susceptibility to chronic cases of infection.

The algal biomass can be used to affect the viability of the pathogens causing the infection and the resulting inflammation and loss of function by the above method regardless of the source that causes it. Not wishing to be bound by any particular theory, it is believed that by administering a refined extract of algal biomass or bioactive compounds thereof, tighter cell junctures are promoted to mechanically prevent pathogens/bacteria from establishing itself behind the epithelial cells that form the physical boundary of the mammary duct. The effect of inflammatory cytokines and chemokines that are created and/or transported to the site of an infection are inhibited or attenuated. Also, vascular tissue transport is modified, which may restore function. While any dosage form can be used in this method, a preferred dosage form can be topical or intramammary.

In various embodiments, a method of treating bovine mastitis in a dairy cow comprises administering to the animal in need thereof a therapeutically effective amount of an algal biomass derived from at least one *klebsormidium* algae species. For example, the at least one *klebsormidium* algae species comprises *klebsormidium nitens*.

In other aspects, a method of treating bovine mastitis in a dairy cow comprises administering to the animal in need thereof a therapeutically effective amount of a concentrated, sterilized extract of an algal biomass derived from at least one *klebsormidium* algae species. In various embodiments, the at least one *klebsormidium* algae species comprises *klebsormidium nitens*.

A method of treating bovine mastitis in a dairy cow may also comprise administering to the animal in need thereof a therapeutically effective amount of a supernatant obtained from the drying of at least one *klebsormidium* algae species. In various embodiments, the at least one *klebsormidium* algae species comprises *klebsormidium nitens*.

A method of treating bovine mastitis in a dairy cow may comprise administering to the animal in need thereof a therapeutically effective amount of at least one of an extract, derivative and biologically active compound derived from an algal biomass further derived from at least one *klebsormidium* algae species. In various embodiments, the at least one *klebsormidium* algae species comprises *klebsormidium nitens*.

Methods of Treating Bovine Respiratory Disease Complex:

In various embodiments, a method of treating bovine respiratory disease complex in a beef or dairy cow comprises administering to the animal in need thereof a therapeutically effective amount of an algal biomass derived from at least one species of algae. Further, a method of treating bovine respiratory disease complex in a beef or dairy cow comprises administering to the animal in need thereof a therapeutically effective amount of a composition comprising an algal biomass derived from at least one species of algae. In various embodiments, a method of treating bovine respiratory disease complex in a beef or dairy cow comprises administering to the animal in need thereof a therapeutically effective amount of a supernatant obtained from drying at least one species of algae. In various embodiments, a method of treating bovine respiratory disease complex in a beef or dairy cow comprises administering to the animal in need thereof a therapeutically effective amount of at least one of an extract, derivative and biologically active compound derived from an algal biomass further derived from at least one species of algae. In various embodiments, the at least one species of algae comprises a *klebsormidium* species of algae. In various embodiments, the at least one species of algae is selected from the group consisting of *klebsormidium nitens, klebsormidium flaccidum,* and mixtures thereof. In various embodiments, the at least one species of algae comprises *klebsormidium nitens*. In various embodiments, the at least one species of algae comprises *klebsormidium flaccidum*.

Administering a therapeutically effective amount of an algal biomass or supernatant derived from at least one species of algae, or administering a therapeutically effective amount of at least one of an extract, derivative and biologically active compound derived from an algal biomass, to a beef or dairy cow in need thereof can modulate the autoimmune system and/or treats inflammation in the cattle. In various embodiments, an algal biomass derived from *klebsormidium nitens* is administered.

Bovine respiratory disease complex (also called "Shipping Fever") is caused by many factors, including weaning, transport, change in feed, commingling, crowding, dust, inadequate ventilation, variations in temperature, and pathogens present either before or after crowding with other animals. The pathogens can include, but are not limited to, Bovine Respiratory Syncytial Virus (BRSV), ParaInfluenza 3 (PI3), Adenovirus, Bovine Viral Diarrhea Virus (BVDV), Infectious Bovine Rhinotracheitis (IBR), *Pasteurella multocida, Mannheimia haemolytica, Histophilus somni, Mycoplasma bovis,* lungworms, or fungus.

Regardless of the source of the bovine respiratory disease complex, a method of treating the disease comprises administration of a therapeutically effective amount of an algal biomass derived from at least one species of algae. Not wishing to be bound by any particular theory, it is believed that by administering an algal biomass, tighter cell junctures can be promoted for epithelial cells surrounding any opening to the environment (nose, mouth, eyes, etc.). The effect of inflammatory cytokines and chemokines that are created or transported to the site of an infection are thus inhibited or attenuated by the tighter junctions. Also, vascular tissue transport is likely modified.

In exemplary aspects, a method of treating bovine respiratory disease complex in a beef or dairy cow comprises administering to the animal in need thereof a therapeutically effective amount of an algal biomass derived from at least one *klebsormidium* algae species. In various embodiments, the at least one *klebsormidium* algae species comprises *klebsormidium nitens*.

Furthermore, a method of treating bovine respiratory disease complex in a beef or dairy cow comprises administering to the animal in need thereof a therapeutically effective amount of a concentrated, sterilized extract of an algal biomass derived from at least one *klebsormidium* algae species. In various embodiments, the at least one *klebsormidium* algae species comprises *klebsormidium nitens*.

In other examples, a method of treating bovine respiratory disease complex in a beef or dairy cow comprises administering to the animal in need thereof a therapeutically effective amount of a supernatant obtained from the drying of at least one *klebsormidium* algae species. In various embodiments, the at least one *klebsormidium* algae species comprises *klebsormidium nitens*.

A method of treating bovine respiratory disease complex in a beef or dairy cow may comprise administering to the animal in need thereof a therapeutically effective amount of at least one of an extract, derivative and biologically active compound derived from an algal biomass further derived from at least one *klebsormidium* algae species. For example, the at least one *klebsormidium* algae species may comprise *klebsormidium nitens*.

Methods of Reducing Pain, and Discomfort Caused By Osteoarthritis, Slight to Moderate Injury Or Overexertion Or Muscle and Connective Tissue Strains in Animals:

The disclosure further provides a method of reducing pain, and discomfort caused by osteoarthritis, slight to moderate injury or overexertion or muscle and connective tissue strains in animals comprising administering to the animal in need thereof a therapeutically effective amount of an algal biomass derived from at least one species of algae. In various embodiments, a method of reducing pain, and discomfort caused by osteoarthritis, slight to moderate injury or overexertion or muscle and connective tissue strains in animals comprises administering to the animal in need thereof a therapeutically effective amount of a composition comprising an algal biomass derived from at least one species of algae. Also, a method of reducing pain, and discomfort caused by osteoarthritis, slight to moderate injury or overexertion or muscle and connective tissue strains in animals comprises administering to the animal in need thereof a therapeutically effective amount of a supernatant obtained from drying at least one species of algae. In various embodiments, a method of reducing pain, and discomfort caused by osteoarthritis, slight to moderate injury or overexertion or muscle and connective tissue strains in animals comprises administering to the animal in need thereof a therapeutically effective amount of at least one of an extract, derivative and biologically active compound derived from an algal biomass further derived from at least one species of algae. Also, the animal in need of treatment thereof is a dog. In various embodiments, the at least one species of algae comprises a *klebsormidium* species of algae. For example, the at least one species of algae may be selected from the group consisting of *klebsormidium nitens, klebsormidium flaccidum,* and mixtures thereof. In other embodiments, the at least one species of algae comprises *klebsormidium nitens*. Further, the at least one species of algae may comprise *klebsormidium flaccidum*.

Not wishing to be bound to any particular theory, it is believed that the algal biomass reduces or eliminates inflammation or discomfort, and slight or moderate loss of function at joints in the animal over time by inhibiting or attenuating the production or transport of pro-inflammatory interleukins, effectively preventing them from attacking and degrading cartilage in the joint. Metabolized or otherwise isolated components of the algal biomass extract may also support joint health by preventing glycosaminoglycan (GAG) loss associated with osteoarthritis. Any suitable dosage form can be used.

Also provided is a method of reducing pain, and discomfort caused by osteoarthritis, slight to moderate injury or overexertion or muscle and connective tissue strains in a human comprising administering to the human subject in need thereof a therapeutically effective amount of an algal biomass derived from at least one species of algae. In various embodiments, a method of reducing pain, and discomfort caused by osteoarthritis, slight to moderate injury or overexertion or muscle and connective tissue strains in a human comprises administering to the human subject in need thereof a therapeutically effective amount of a composition comprising an algal biomass derived from at least one species of algae. Furthermore, a method of reducing pain, and discomfort caused by osteoarthritis, slight to moderate injury or overexertion or muscle and connective tissue strains in a human comprises administering to the human subject in need thereof a therapeutically effective amount of a supernatant obtained from drying at least one species of algae. In various embodiments, a method of reducing pain, and discomfort caused by osteoarthritis, slight to moderate injury or overexertion or muscle and connective tissue strains in a human comprises administering to the human subject in need thereof a therapeutically effective amount of at least one of an extract, derivative and biologically active compound derived from an algal biomass further derived from at least one species of algae. In various embodiments, the at least one species of algae comprises a *klebsormidium* species of algae. In various embodiments, the at least one species of algae is selected from the group consisting of *klebsormidium nitens, klebsormidium flaccidum,* and mixtures thereof. In various embodiments, the at least one species of algae comprises *klebsormidium nitens.* In various embodiments, the at least one species of algae comprises *klebsormidium flaccidum.* In various embodiments, an algal biomass administered to a human subject in need of treatment thereof reduces or eliminates inflammation at joints in the human over time.

Not wishing to be bound by any particular theory, it is believed that by administering the algal biomass its extracts or isolates to humans, pro-inflammatory interleukins are inhibited from attacking and degrading cartilage in the joint. Metabolized or otherwise isolated components of the algal biomass extract may also support joint health by preventing glycosaminoglycan (GAG) loss associated with osteoarthritis.

EXAMPLES

Example 1. Preparation of an Algal Biomass (Single Culture to Small Culture):

A sample of NCMA Deposit # PATENT201602001 was used to grow algae axenically on an mBBM agar petri plate. A single colony was picked from the plate and grown in mBBM media in a shake flask for one month to achieve adequate density for roux bottle inoculation. Algae inoculum grown in roux bottles was progressively divided to produce the minimum inoculation density required for panel reactor growth. Algae biomass grown in reactors was placed in a 25 µm filter sock to remove supernatant using gravity flow. Excess supernatant was removed with manual squeezing of the filter sock until the consistency of the algal biomass reached a thick paste. The algal biomass was then spread into a ½ inch layer on a stainless steel tray and placed at −80° C. until frozen. The tray was then moved to a vacuum equipped freeze-drier, and the material held at −50° C. to −60° C. for several days until the moisture level was reduced to about 5 to 10% by weight. The freeze-dried algal biomass was stored in a refrigerator at 4° C. or in a freezer at −20° C. until use.

Example 2. Preparation of an Algal Biomass (Scale-Up of Small Culture):

Monocultures of a filamentous alga are grown in 120 L and 240 L flat panels with a 4-inch light path, 3-9 mM $NO_3$ in mBBM media, and $CO_2$/air mixing or within outdoor, covered, HEPA filtered ponds using natural light. Harvesting consist of drawing off the liquid and algae that is contained in the liquid and separating the liquid from the algal biomass. There is typically about 1.4 grams of algae per liter of water. Upon harvesting, biomass is placed in a 25 µm filter sock to remove water using gravity flow. Excess water is removed with manual squeezing resulting in a wet paste that is about 15% solids and 85% water. The appearance of the biomass is that of a bright green thick paste. On average, about 8-10 kg wet weight yields about 1 kg of algal biomass in the form of a paste. This material is then spread onto stainless steel trays in a ½" layer and placed in a −80° C. freezer until frozen or ready for further processing. Freeze dried biomass is achieved by placing the tray in a freeze-drier equipped with a vacuum pump and set at −50° C. to −60° C. for several days until the moisture level was reduced to 5-10%. Freeze-dried biomass was stored in a refrigerator at 4° C. or freezer at −20° C. until use. The freeze dried algal biomass material produced in accordance to this method effectively has no water and is in the form of a dark green powder or a brittle cake.

Example 3. Treatment of Bovine Mastitis by Oral ("ORAL") Administration of an Algal Biomass.

A pilot examination of a treatment targeting Mycoplasma bovis in dairy cows with mastitis was conducted at a commercial research facility to demonstrate the use of algal biomass and supernatant as method of treating bovine mastitis in dairy cows. A Mycoplasma bovis strain isolate from a dairy cow herd with naturally occurring bovine mastitis was used to inoculate one quarter per animal to induce clinical mastitis using an experimental infection model previously proven to be successful. The algal biomass prepared in accordance to Example 2 was removed from cold storage immediately prior to use. Three ounces of algal biomass was suspended in a small amount of distilled water such that it was administrable to an animal orally. This unrefined and minimally processed algal biomass was administered orally (ORAL) to a group of eight cows once a day for eight (8) days via an administration gun equipped with a syringe loaded with 3 oz. of the suspended algal biomass for each dosage.

Example 4. Preparation of a Supernatant.

Monocultures of a filamentous alga are grown in 120 L and 240 L flat panels with a 4-inch light path, 3-9 mM $NO_3$ in mBBM media, and $CO_2$/air mixing or within outdoor, covered, HEPA filtered ponds using natural light. Harvesting consist of drawing off the liquid and algae that is contained in the liquid and separating the liquid from the algal biomass. There is typically about 1.4 grams of algae per liter of water. Upon harvesting, supernatant is collected as the harvest is passed through a 25 µm filter sock until it is clear of algae. The clarified supernatant is transferred to previously-sanitized 60 gal barrels and stored at 4° C. until filtration and concentration. The appearance of the clarified supernatant is that of a clear liquid (i.e., water). Supernatant is concentrated anywhere from 10 to 500 times (i.e. 10× to 500×) using a rotary evaporator. The appearance of concentrated supernatant varies with degree of concentration, from a clear liquid having the consistency of regular tap water, to a yellow, viscous, syrup-like liquid in higher concentrations.

Example 5. Treatment of Bovine Mastitis By Intramammary Intubation ("IMM") and Subcutaneous ("SQ") Administration of a Supernatant.

A pilot examination of a treatment targeting *Mycoplasma bovis* in dairy cows with mastitis was conducted at a commercial research facility to demonstrate the use of algal biomass and supernatant as method of treating bovine mastitis in dairy cows. A *Mycoplasma bovis* strain isolate from a dairy cow herd with naturally occurring bovine mastitis was used to inoculate one quarter per animal to induce clinical mastitis using an experimental infection model previously proven to be successful. The supernatant prepared in Example 4, having a syrup-like consistency after concentration, was diluted with sterile water to produce an injectable liquid. As in Example 2, cows were inoculated with *Mycoplasma bovis* pathogen and exhibited clinical mastitis. The injectable liquid thus prepared was administered either by intramammary intubation ("IMM") (group of 9 subjects) or subcutaneous injection ("SQ") (group of 9 subjects) over the course of eight (8) days. IMM animals were administered 20 mL 100× supernatant, and the SQ animals were administered 30 mL 100× supernatant, both once a day for eight days at 24 h apart. IMM utilized a syringe with sterile teat cannula. SQ utilized a syringe with a sterile needle.

Results (a) Milk Appearance. There was a statistically significant improved milk appearance score (color and consistency) in the IMM group. By study end, 7 out of 9 animals, or 78% of the IMM treated animals, had normal milk production versus the non-treated group that had 1 out of 8, or 13%. There was a tendency for improvement (albeit not statistically significant) in the SQ and ORAL groups. By study end, there were 6 out of 9 animals (67%) that were producing normal milk in the SQ group and 4 out of 8 animals (50%) in the ORAL group. Hazard Ratio (HR) estimates with (95% CI) of treatment effect using NO TX as a reference for cows receiving IMM supernatant had a 13.3 (1.6, 109.4) times higher hazard rate to have normal milk appearance score compared to cows receiving NO TX (P=0.016). The HR for ORAL was 6.9 (0.8, 58.8), and for SQ was 6.7 (0.8, 55.6), and both tended to be significantly different from 1 (P=0.075).

(b) Fewer Excessively Abnormal Milk Samples of Dry Quarters. Toward the end of the study, milk samples from much of the untreated group could not be assessed for milk appearance or quality because the milk had become excessively abnormal or the quarters were dry, in sharp contrast to the IMM, SQ and ORAL groups where milk production largely continued despite infection. There were 11 samples from two cows in the IMM group that could not be assessed, 14 samples from five cows in the SQ group, and 13 samples from three cows in the ORAL group compared to 37 milk samples from the inoculated quarters of six cows that were not treated with any algal biomass or supernatant.

(c) Less Aerobic Bacterial Growth. The SQ and ORAL treated groups had statistically significant reductions in the growth of aerobic bacteria compared to the non-treated group, as well as to the non-inoculated quarters in the IMM group, which were ostensibly untreated.

It will be apparent to those skilled in the art that various modifications and variations can be made to the present disclosure without departing from the spirit or scope of the disclosure. Thus, it is intended that the present disclosure cover the modifications and variations of this disclosure provided they come within the scope of the appended claims and their equivalents.

We claim:

1. A method of modulating inflammation and/or modulating an immune response in a bovine animal relating to bovine mastitis or bovine respiratory disease complex, said method comprising administering to the bovine animal in need thereof a therapeutically effective amount of a composition comprising an algal biomass or a supernatant obtained by processing the biological material of NCMA Deposit # PATENT201602001.

2. The method of claim 1, wherein said composition is a paste further comprising said algal biomass suspended in water.

3. The method of claim 1, wherein said administering comprises oral, subcutaneous, intravenous, and intramammary.

4. The method of claim 1, wherein said composition is an injectable liquid or a liquid for intubation derived from said supernatant.

5. The method of claim 1, wherein the biological material of NCMA Deposit #PATENT201602001 comprises at least one species of *klebsormidium* algae.

6. The method of claim 1, wherein the biological material of NCMA Deposit #PATENT201602001 comprises at least one of *klebsormidium nitens* and *klebsormidium flaccidum* species of algae.

7. A method of modulating inflammation and/or modulating an immune response in a bovine animal caused by a disease or an infection, said method comprising administering to the animal in need thereof a therapeutically effective amount of a composition comprising an algal biomass or a supernatant obtained by processing the biological material of NCMA Deposit # PATENT201602001.

8. The method of claim 7, wherein the biological material of NCMA Deposit #PATENT201602001 comprises at least one species of *klebsormidium* algae.

9. The method of claim 7, wherein the biological material of NCMA Deposit #PATENT201602001 comprises at least one of *klebsormidium nitens* and *klebsormidium flaccidum* species of algae.

10. The method of claim 7, wherein said composition is an injectable liquid or a liquid for intubation derived from said supernatant.

11. The method of claim 7, wherein said composition is a paste further comprising said algal biomass suspended in water.

12. The method of claim 7, wherein the disease or infection is characterized as bovine mastitis or bovine respiratory disease complex.

13. The method of claim 7, wherein said administering comprises oral, subcutaneous injection, or intramammary intubation.

14. The method of claim 7, wherein the processing comprises growing a sample of NCMA Deposit # PATENT201602001 into an algae culture and mechanically separating the algae culture into the algal biomass and the supernatant.

* * * * *